(12) United States Patent
Tatarkiewicz et al.

(10) Patent No.: US 10,012,580 B2
(45) Date of Patent: Jul. 3, 2018

(54) APPARATUS AND METHOD FOR MEASUREMENTS OF GROWTH OR DISSOLUTION KINETICS OF COLLOIDAL PARTICLES

(71) Applicant: MANTA Instruments, Inc., San Diego, CA (US)

(72) Inventors: Jan J. Tatarkiewicz, San Diego, CA (US); Monette Karr, San Diego, CA (US)

(73) Assignee: Manta Instruments, Inc., San Diego, CA (US)

( * ) Notice: Subject to any disclaimer, the term of this patent is extended or adjusted under 35 U.S.C. 154(b) by 0 days.

(21) Appl. No.: 15/293,180

(22) Filed: Oct. 13, 2016

(65) Prior Publication Data

US 2017/0122860 A1    May 4, 2017

Related U.S. Application Data

(63) Continuation-in-part of application No. 15/018,532, filed on Feb. 8, 2016, and a continuation-in-part of (Continued)

(51) Int. Cl.
*G01N 15/02* (2006.01)
*G01N 15/14* (2006.01)
(Continued)

(52) U.S. Cl.
CPC .......... *G01N 15/1463* (2013.01); *G01N 13/00* (2013.01); *G01N 15/0205* (2013.01);
(Continued)

(58) Field of Classification Search
CPC .. G06K 9/36; G06K 9/00; G01N 1/10; G01N 15/02; G01N 31/00; G01N 15/1463;
(Continued)

(56) References Cited

U.S. PATENT DOCUMENTS 6,836,559 B2 * 12/2004 Abdel-Fattah ..... G01N 15/1463
377/10
7,679,742 B2    3/2010 Haddock et al.
(Continued)

OTHER PUBLICATIONS

International Search Report and Written Opinion issued in PCT/US2016/056909 dated Jan. 10, 2017 (16 pages).

*Primary Examiner* — Jamil Ahmed
(74) *Attorney, Agent, or Firm* — Mauel de la Cerra

(57) ABSTRACT

A system for determining the growth/dissolution rate of colloidal particles is disclosed and includes multiple light sources and multiple sensors. A light source is constructed to emit a beam of electromagnetic radiation at a specimen chamber that holds the colloidal particles. The chamber allows a portion of the combined beam to scatter perpendicularly or at some other angle to the combined beam. The scattered portion of the beam is directed to a sensor that detects electromagnetic radiation. The sensor is connected to processor that activates the light source and obtains an image from the sensor. Multiple images are taken at a time interval and for each image taken, and a total image intensity level is calculated and normalized. A formula is then calculated that fits the normalized values over time and a slope is determined from the formula.

23 Claims, 8 Drawing Sheets

Related U.S. Application Data application No. 15/194,823, filed on Jun. 28, 2016, now Pat. No. 9,541,490.

(60) Provisional application No. 62/241,354, filed on Oct. 14, 2015.

(51) Int. Cl.
 *G01N 21/51* (2006.01)
 *G01N 13/00* (2006.01)
 *G01N 15/00* (2006.01)

(52) U.S. Cl.
 CPC ..... *G01N 21/51* (2013.01); *G01N 2015/0038* (2013.01); *G01N 2015/0053* (2013.01); *G01N 2015/0092* (2013.01); *G01N 2015/0277* (2013.01); *G01N 2021/513* (2013.01); *G01N 2201/061* (2013.01); *G01N 2201/12* (2013.01)

(58) Field of Classification Search
 CPC ...... G01N 21/47; G01N 15/1456; G01B 9/02; G01J 3/00; G06F 19/00; B01L 3/0275
 See application file for complete search history.

(56) References Cited

U.S. PATENT DOCUMENTS

| | | | |
|---|---|---|---|
| 2003/0139886 A1* | 7/2003 | Bodzin | G01N 21/47 702/28 |
| 2008/0137080 A1* | 6/2008 | Bodzin | G01N 21/47 356/300 |
| 2009/0323061 A1* | 12/2009 | Novotny | G01N 15/1456 356/336 |
| 2012/0309636 A1* | 12/2012 | Gibbons | B01L 3/0275 506/9 |

* cited by examiner

APPARATUS AND METHOD FOR MEASUREMENTS OF GROWTH OR DISSOLUTION KINETICS OF COLLOIDAL PARTICLES

RELATED APPLICATIONS

This application claims priority to U.S. Provisional Patent Application No. 62/241,354 filed on Oct. 14, 2015, titled "APPARATUS FOR MEASUREMENTS OF GROWTH OR DISSOLUTION KINETICS OF COLLOIDAL NANOPARTICLE". This application also claims priority as a continuation in part of U.S. patent application Ser. No. 15/018,532 filed on Feb. 8, 2016, titled "MULTI-CAMERA APPARATUS FOR OBSERVATION OF MICROSCOPIC MOVEMENTS AND COUNTING OF PARTICLES IN COLLOIDS AND ITS CALIBRATION", and as a continuation in part of U.S. patent application Ser. No. 15/194,823, filed on Jun. 28, 2016, titled "SPECIAL PURPOSE CUVETTE ASSEMBLY AND METHOD FOR OPTICAL MICROSCOPY OF NANOPARTICLES IN LIQUIDS", the disclosures of which are herein incorporated by reference in their entirety.

This application is also related to U.S. patent application Ser. No. 14/730,138, filed on Jun. 3, 2015, titled "NANOPARTICLE ANALYZER" the disclosure of which is herein incorporated by reference in its entirety.

TECHNICAL FIELD

The present invention relates to measurements and observations of particles in liquid samples using a microscope equipped with digital video cameras.

BACKGROUND

Nanoparticles (particles with diameters smaller than 1 micron) are ubiquitous and by far the most abundant particle-like entities in natural environments on Earth and are widespread across many applications associated with human activities. There are many types of naturally occurring nanoparticles and man-made (engineered) nanoparticles. Nanoparticles are found in the air, in aquatic environments, in rain water, in drinking water, in bio-fluids, in pharmaceuticals, and in drug delivery and therapeutic products, and a broad range of many industrial products. Nanoparticles usually occur within poly-disperse assemblages, which are characterized by co-occurrence of differently-sized particles, including those larger in thediameter than 1 micron.

Given the widespread usage of nanoparticles, the ability to control and accurately characterize their properties may be useful to many applications. Conventional methods for measuring nanoparticle properties may be inaccurate for poly-disperse samples of mixed nanoparticle sizes, which are common in many applications. Because the light scattered from all nanoparticles is measured simultaneously, it may be difficult to resolve the nanoparticles into their constituent sizes when there is a range of particle sizes. Other approaches fail to account for the large differences in the intensity of scattered light produced by differently-sized nanoparticles across the range of nanoparticle sizes. In these approaches, the low scattering signals from small nanoparticles may be undetected, or the high scattering signals from larger nanoparticles can obscure the signals from smaller nanoparticles. And in yet other approaches, the measurements fail to account for the growth rate or dissolution rate of the particles, such that a snap-shot of a size distribution could be inaccurate a few moments later. As a result of these deficiencies, the concentration of nanoparticles of any given size, and hence the entire size distribution, can be subject to unknown error.

These methods of detecting nanoparticles (and larger particles) are commonly referred as dark field microscopy. The instrument to perform such an analysis typically comprises a small cell (for example a cuvette) that enables illumination of a liquid with a precisely-defined, narrow light sheet and observation of the scattered light from the nanoparticles, usually (but not necessarily) at a 90-degree angle relative to the light sheet plane. It should be noted that the angle of observation need not be 90 degrees; what is important is that the scattered light is observed. Different sizes of particles can be visualized via the camera capturing light scattered by particles, with images having different sizes and intensities (various brightness of pixels) depending on the size of the particles.

In U.S. patent application Ser. No. 14/730,138, filed on Jun. 3, 2015, titled "NANOPARTICLE ANALYZER" ("Stramski"), the entirety of which is incorporated herein by reference, these problems were addressed by using several light sources and a single-color camera recording simultaneously several different colors of scattered light by the Bayer pattern of pixels corresponding to the three additive primary colors conventionally used in photography. In the Stramski approach, final images were obtained from a single recording device, and hence images of the same colloidal volume at different colors were recorded in the same area of the recording device or sensor, thereby resulting in pixel numbering relative to a single point of origin, usually being one of the corners of a sensor in the camera. This made processing images in different colors possible because positions of observed particles were given in the same system of coordinates. Unfortunately, Stramski does not discuss or disclose any methods to account for the growth or dissolution of the particles.

U.S. application Ser. No. 15/018,532 filed on Feb. 8, 2016, titled "MULTI-CAMERA APPARATUS FOR OBSERVATION OF MICROSCOPIC MOVEMENTS AND COUNTING OF PARTICLES IN COLLOIDS AND ITS CALIBRATION" ("Tatarkiewicz") overcomes some of the deficiencies of Stramski by introducing a calibration mask and method that can align the images from various light sources such that processing of the images is made more accurate. But again, Tatarkiewicz does not discuss or disclose any methods to account for the growth or dissolution of the particles.

The growth/dissolution of particles can be of particular interest is various industries. For example, a pharmaceutical company may want to confirm that its drug dissolves at a particular rate such that it can be used in an effective time-release mode. Moreover, such a dissolution may be most therapeutically effective when the particles dissolve to the nanoscale and does not re-combine to grow into larger particles. Another pharmaceutical company may need to determine the time needed to crystallize a new drug based on protein that can be delivered in higher doses as large crystals. So, while the methods and apparatuses disclosed in Stramski and Tatarkiewicz may be helpful in obtaining a snapshot of the particle size distribution of the drug, it is not helpful in providing a dissolution rate (or conversely a growth rate).

What is needed, therefore, is an improved system that effectively measures the growth/dissolution kinetics of colloidal particles.

SUMMARY

The following presents a simplified summary in order to provide a basic understanding of some aspects of the claimed subject matter. This summary is not an extensive overview and is not intended to identify key/critical elements or to delineate the scope of the claimed subject matter. Its purpose is to present some concepts in a simplified form as a prelude to the more detailed description that is presented later.

The apparatus, systems, and methods described herein elegantly solve the problems presented above. A system for determining the growth/dissolution rate of colloidal particles is disclosed and includes multiple light sources and multiple sensors. A light source is constructed to emit a beam of electromagnetic radiation at a specimen chamber that holds the colloidal particles. The chamber allows a portion of the combined beam to scatter. The scattered portion of the beam is directed to a sensor that detects electromagnetic radiation. The sensor is connected to processor that activates the light source and obtains an image from the sensor. Multiple images may be taken at a time interval, and, for each image, a total light intensity level (sum of all intensities registered at all pixels) is calculated and then normalized by the maximum intensity level in the sequence. An average intensity value from multiple images is obtained for each time point. A formula is then calculated that fits the normalized values over time and a slope is determined from the formula. Also, instead of still images at a particular time interval, a short set of images (i.e., a video) may be taken at the time interval. An average of the sum of intensities for each video and for each time interval is calculated and then normalized by the maximum intensity level in the sequence.

The processor may also set a measurement window that limits how many images will be taken. That measurement window may be based on a total elapsed time or total number of images obtained. It can also be based on the slope that is calculated. The processor may further set a maximum image intensity level and adjust the exposure time of the sensors when the total image intensity level exceeds the maximum intensity level.

The apparatus may use multiple light sources with multiple wavelengths, and multiple sensors that are biased in detecting only one of the multiple wavelengths. The system may use combining structures to form the combined beam and de-combining structures (or beam splitters) before the scattered beam portion reaches the sensors. The multiple light sources may be a single multi-wavelength light source. The sensors may also be a single sensor that can detect multiple wavelengths.

If the slope as calculated is negative, it indicates dissolution of the colloidal particles, and if it is positive it indicates growth of the colloidal particles.

Additional aspects, alternatives and variations as would be apparent to persons of skill in the art are also disclosed herein and are specifically contemplated as included as part of the invention. The invention is set forth only in the claims as allowed by the patent office in this or related applications, and the following summary descriptions of certain examples are not in any way to limit, define or otherwise establish the scope of legal protection.

BRIEF DESCRIPTION OF THE DRAWINGS

The invention can be better understood with reference to the following figures. The components within the figures are not necessarily to scale, emphasis instead being placed on clearly illustrating example aspects of the invention. In the figures, like reference numerals designate corresponding parts throughout the different views and/or embodiments. It will be understood that certain components and details may not appear in the figures to assist in more clearly describing the invention.

DETAILED DESCRIPTION

Figure 1A:
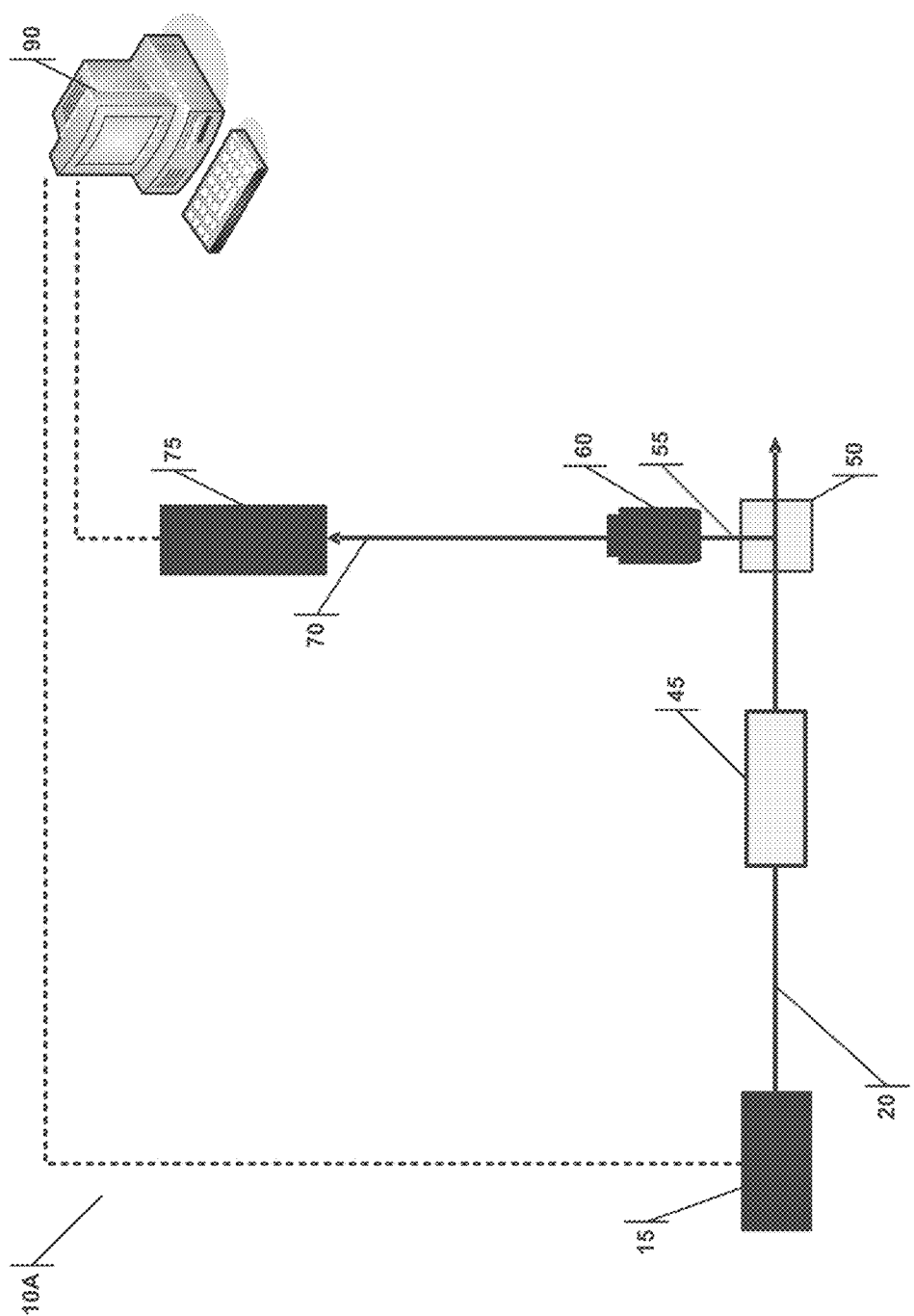
FIG. 1A illustrates a system for detecting electromagnetic radiation from a cuvette using a single wavelength source.

Reference is made herein to some specific examples of the present invention, including any best modes contemplated by the inventor for carrying out the invention. Examples of these specific embodiments are illustrated in the accompanying figures. While the invention is described in conjunction with these specific embodiments, it will be understood that it is not intended to limit the invention to the described or illustrated embodiments. To the contrary, it is intended to cover alternatives, modifications, and equivalents as may be included within the spirit and scope of the invention as defined by the appended claims.

In the following description, numerous specific details are set forth in order to provide a thorough understanding of the present invention. Particular example embodiments of the present invention may be implemented without some or all of these specific details. In other instances, process operations well known to persons of skill in the art have not been described in detail in order not to obscure unnecessarily the present invention. Various techniques and mechanisms of the present invention will sometimes be described in singular form for clarity. However, it should be noted that some embodiments include multiple iterations of a technique or multiple mechanisms unless noted otherwise. Similarly, various steps of the methods shown and described herein are not necessarily performed in the order indicated or performed at all in certain embodiments. Accordingly, some implementations of the methods discussed herein may include more or fewer steps than those shown or described. Furthermore, the techniques and mechanisms of the present invention will sometimes describe a connection, relationship or communication between two or more entities. It should be noted that a connection or relationship between entities does not necessarily mean a direct, unimpeded connection, as a variety of other entities or processes may reside or occur between any two entities. Consequently, an indicated connection does not necessarily mean a direct, unimpeded connection unless otherwise noted.

The following list of example features corresponds with FIGS. 1-4 and is provided for ease of reference, where like reference numerals designate corresponding features throughout the specification and figures:

A system for detecting electromagnetic radiation from a cuvette using a single wavelength 10A.
A system for detecting electromagnetic radiation of multiple wavelengths 10B.
An alternate system for detecting electromagnetic radiation of multiple wavelength 10C.
Light source 15.
First light source at a first wavelength 15A.
Beam of electromagnetic radiation emitted from the light source 20.
First beam of electromagnetic radiation at substantially a first wavelength 20A.
Second light source at a second wavelength 25.
Second beam of electromagnetic radiation at substantially a second wavelength 30.
A third light source at a third wavelength 32.
Third beam of electromagnetic radiation at substantially a third wavelength 34.
Beam combining structure/dichroic mirror 35.
A second beam combining structure/dichroic mirror 37.
Combined beam 40.
Light sheet former 45.
Specimen chamber/cuvette 50.
Scatter light 55.
A portion of the third beam that scatters 55A.
Imaging objective 60.
Beam splitting structure/dichroic mirror 65.
Scatter beam directed onto image sensor 70.
Separated first wavelength radiation 70A.
Image sensor. 75
First sensor biased to detect electromagnetic radiation at substantially the first wavelength 75A.
Separated second wavelength radiation 80.
Second sensor biased to detect electromagnetic radiation at substantially the second wavelength 85.
Separated third wavelength radiation 86.
Third sensor biased to detect electromagnetic radiation at substantially the third wavelength 87.
Second beam splitting structure/dichroic mirror 88.
Processor 90.
Best fit line with constant slope 95.
Best fit line with varying slope 100.
Method for determining the growth/dissolution rate of colloidal particles 405.
Various steps to method 410-500.

With reference to FIG. 1A, a system 10A for detecting electromagnetic radiation from a cuvette is shown. The system 10A includes a single light source 15 that emits at beam of electromagnetic radiation 20 at a light sheet former 45. The resultant light sheet is directed at the specimen chamber/cuvette 50 that houses a colloid containing particles, i.e. nanoparticles or micron-sized particles (not shown). Such a cuvette may be constructed according to U.S. patent application Ser. No. 15/194,823, filed on Jun. 28, 2016, titled "SPECIAL PURPOSE CUVETTE ASSEMBLY AND METHOD FOR OPTICAL MICROSCOPY OF NANOPARTICLES IN LIQUIDS", the contents of which are incorporated herein by reference.

A portion of the light sheet scatters 55 upon impacting the particles present in the colloid solution contained within the cuvette 50, and this can typically be observed at a 90-degree angle by focusing an imaging objective 60, such as a microscope equipped with another long working distance objective. It should be noted that the angle of observation need not be at 90 degrees; what is important is that the scattered light is observed. The scattered light exiting the imaging objective 60 reaches the sensors 75, which is connected to a processor 90.

Figure 1B:
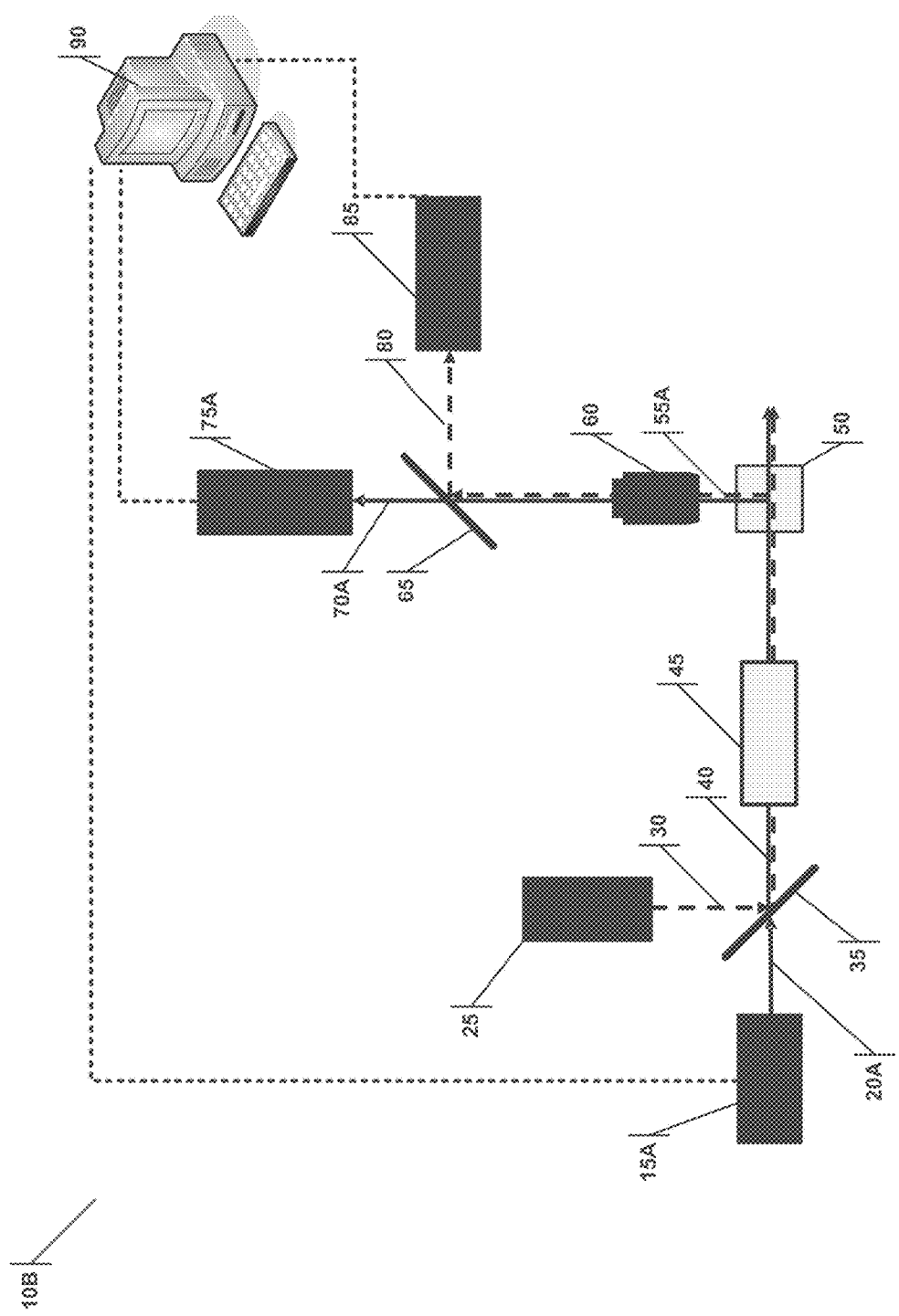
FIG. 1B illustrates a system for detecting electromagnetic radiation of two wavelengths.
Figure 1C:
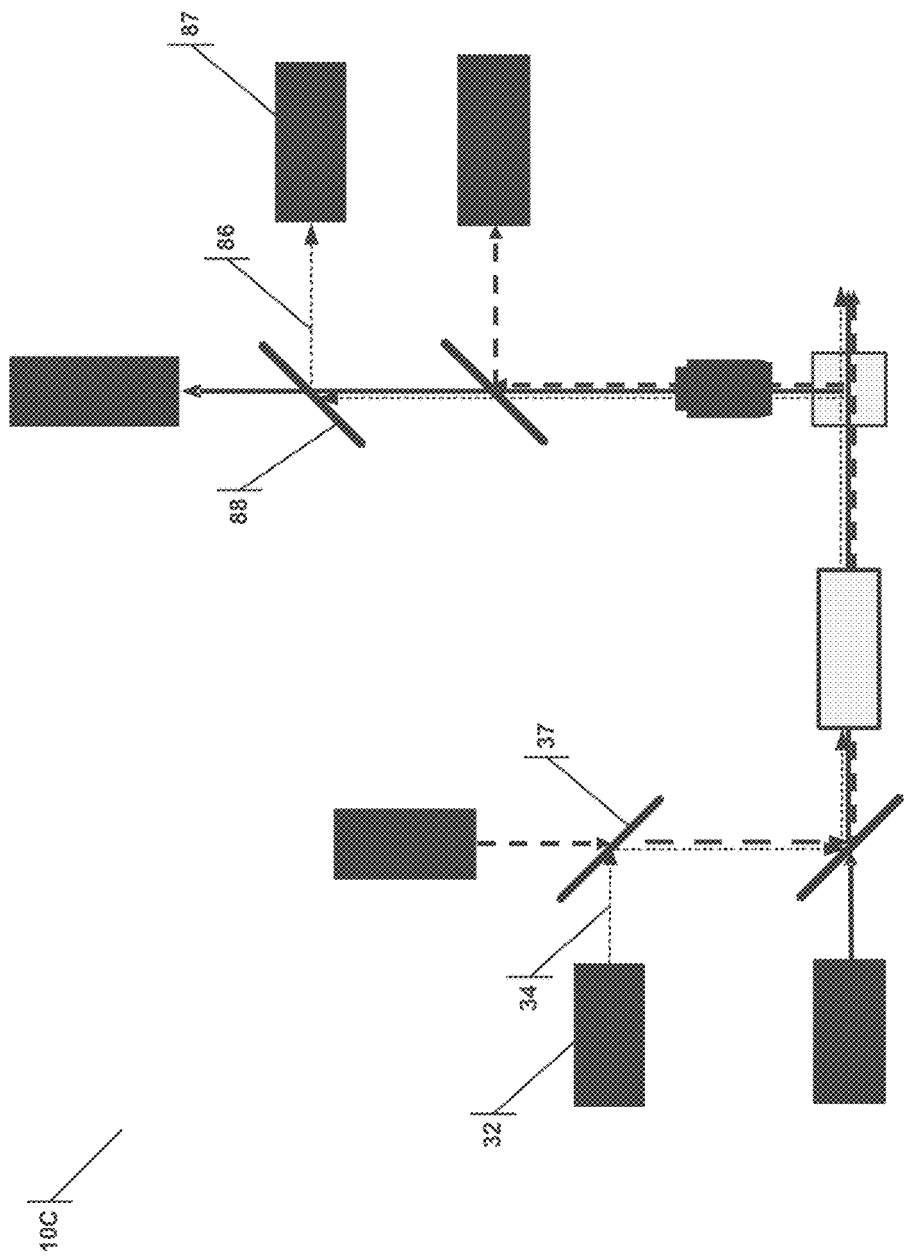
FIG. 1C illustrates a system for detecting electromagnetic radiation of three wavelengths.

FIGS. 1B and 1C illustrate using different wavelengths and wavelength sensors to arrive at a more robust system. The benefit of using multiple wavelengths of light is that is extends the range of particles sizes that can be detected. Specifically, the intensity of scattered light depends very strongly on particle size, changing by many orders of magnitude between 10 nm and 1000 nm diameter nanoparticles, for instance. A typical sensor assigns 8 bits or 256 different values to each pixel and each color, zero value corresponding to no light registered while the highest value of 255 corresponding to the maximum brightness that depends on the gain and exposure set up for the system. If any pixel receives more light than the maximum level corresponding to the value 255 (saturation), it is not possible to distinguish and register such a value except by lowering detector gain or shortening exposure time, thus shifting all recorded intensities into lower values. While lowering gain or shortening exposure may assist in distinguishing particles that have saturated the sensor, these adjustments also lower the sensitivity of the sensor on the bottom end of the spectrum—i.e., the smaller particles.

Figure 2:
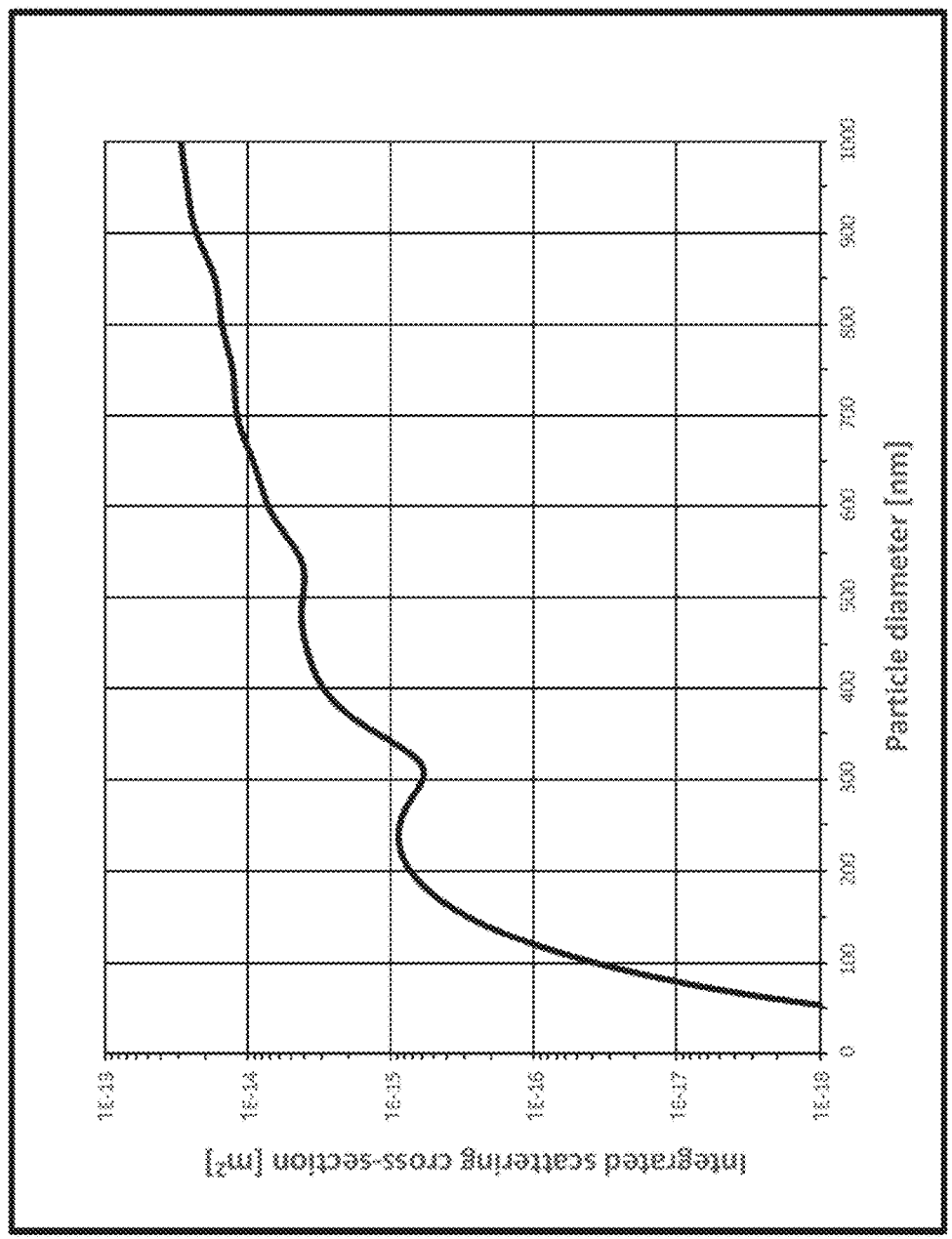
FIG. 2 is a graph showing the scattering coefficient vs. the diameter of a particle.

Because a typical size of nanoparticles (diameter below 1 micron) is comparable with the wavelength of visible light, the system is not able to distinguished details of light scattering nanoparticles but records only total intensity of light scattered, with each particle projecting an image that looks like a circular blob or disc that covers several pixels in the sensor. The intensity of visible light scattered on nanoparticles is depicted in FIG. 2 as the function of the diameter of scattering particles for one wavelength and one type of particle with a specific refractive index (calculations were performed using the so-called Mie theory of scattering at a 90-degree angle for 450 nm light wavelength and polystyrene spheres with refractive index n=1.6 in water). For particles with diameter below 100 nm the scattered intensity becomes very small and is hard to detect.

Moreover, the scatter efficiency of a particle depends on the wavelength of the exposed light; thus, the range of detection depends on the wavelength. By using multiple light sources with different wavelengths and detecting those wavelengths separately (for example 3 colors: red, green and blue, as taught in Stramski and Tatarkiewicz), the operator can substantially extend the dynamic range of the system by covering a broader a range of particle sizes registered.

Referencing FIG. 1B, an example apparatus is shown that uses multiple wavelengths as described in Tatarkiewicz, incorporated herein by reference. Such a system 10B may include a first light source at a first wavelength 15A and a second light source at a second wavelength 25, such as two lasers with different beam colors or wavelengths. It is also possible to have a single light source that is capable of producing light at multiple wavelengths.

Each of these two beams is directed at a combining structure 35, such as a dichroic mirror, which combines the beams from light sources 15, 25 into a single combined beam 40 and directs the combined beam 40 to an optical system, such as a light sheet former 45. The light sheet former 45 may comprise a cylindrical lens together with a long working distance objective that forms a very narrow sheet of illumination. The light sheet may be directed to a transparent specimen chamber 50 (such as a cuvette).

A portion of the combined beam that scatters 55A upon impacting the particles present in the colloid solution contained within the cuvette 50 has the same wavelengths as the illuminating light from the light sheet former 45, and this scattering can typically be observed at a 90-degree angle by focusing an imaging objective 60, such as a microscope equipped with another long working distance objective. It should be noted that the angle of observation need not be at 90-degrees; what is important is that the scattered light is observed. The scattered light exiting the imaging objective 60 is split into constituent wavelengths at a beam splitting structure 65 such as a second dichroic mirror, namely the separated first wavelength radiation 70A and the separated second wavelength radiation 80, that may independently reach the two sensors 75A, 85 (such as those disposed within digital grey-scale cameras), attuned to detect electromagnetic radiation at substantially the first and second wave lengths 15A, 25, respectively. The two sensors can also be a single sensor that can detect electromagnetic radiation at multiple wavelengths.

The system can be easily extended into more wavelengths and more corresponding sensors 75A, 85 by adding more pairs of appropriate dichroic mirrors 35, 65 to combine and split more wavelengths of illuminating light sources 15, 25. Such an example system 10C is shown in FIG. 1C, which illustrates a three-wavelength system with a third light source at a third wavelength 32, that produces a third beam of electromagnetic radiation at substantially a third wavelength 34, and a second combining structure/dichroic mirror 37. On the detection side of the system 10A, a second beam splitting structure/dichroic mirror 88 separates a third wavelength radiation 86 such that it can be detected by a third sensor biased to detect electromagnetic radiation at substantially the third wave length 87. The sensors (75A, 85 and 87) may be connected to a processor 90 that processes the images detected by the sensors (75A, 85 and 87).

As mentioned before, a sensor records the image intensities as a number for each pixel, and each wavelength, typically assigning an 8-bit number (corresponding to 256 different values) to each pixel and each wavelength, with a zero value corresponding to no light registered while the highest value of 255 corresponding to the maximum brightness. The final image taken from the sensors consists of a matrix of numbers stored, corresponding to all pixels available on the sensors, typically more than 1 million of them. By adding all these numbers, a total brightness of the image as a single number can be obtained (separately for each wavelength when more than one wavelength is used). By taking images at preselected times, usually at fixed time intervals, a sequence of numbers can be obtained representing a time evolution of light intensity scattered by particles, which in turn is proportional to the number and size of particles present in the colloid being analyzed.

Figure 3A:
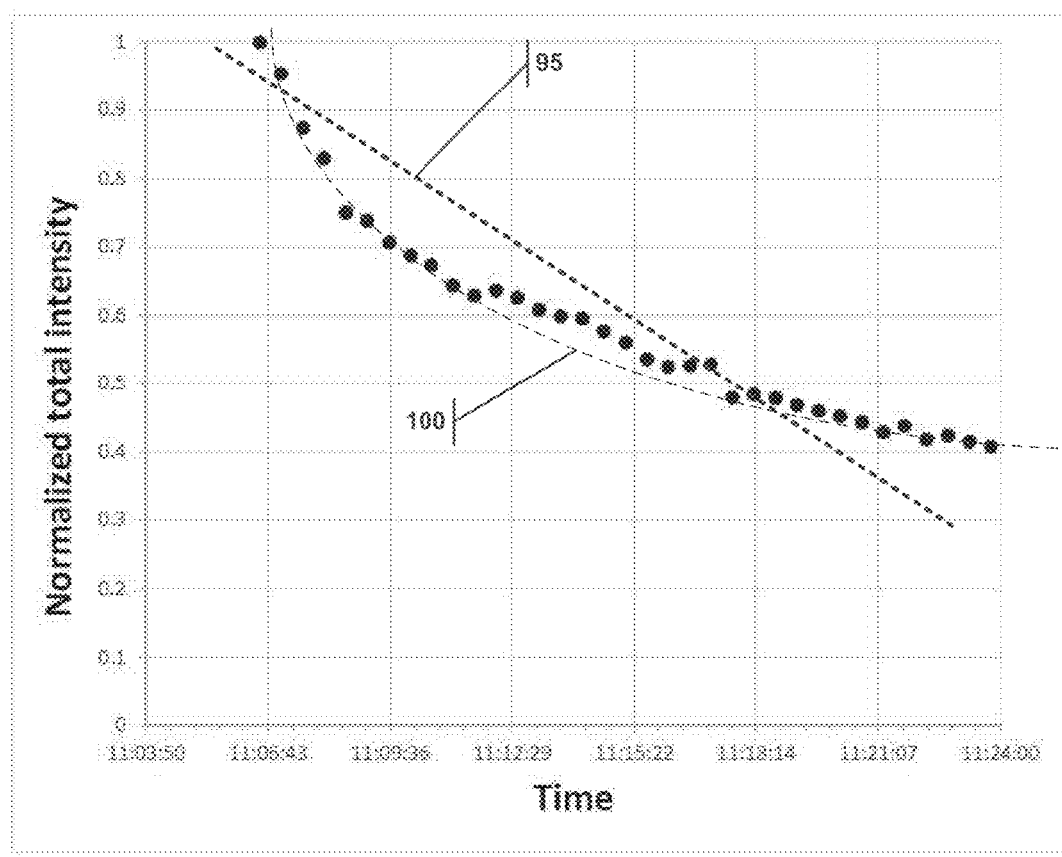
FIG. 3A is a graph showing the normalized total intensity of the particles in a colloidal solution vs. time, illustrating dissolution.

Plotting such values after normalization to the initial value vs. time as shown in FIG. 3A enables estimation of rate of dissolution or growth of number and size of particles (i.e., kinetics) of the process of present in the colloid and undergoing dissolution or growth due to some chemical or physical processes. Line 95 is a best fit for the graph, and the slope of that line is negative—indicating dissolution. Also, the slope of line 95 represents a single average growth/dissolution rate across the entire observed time. A more sophisticated line 100 may fit the data which varies in slope over time—for example line 100 has a steep slope for the first minute that becomes less severe in the latter minutes. This suggests that the colloidal solution is dissolving rapidly for the first minute and less rapidly thereafter. Fully characterizing the growth/dissolution rate can be extremely helpful in industrial applications, such as pharmaceuticals. The slope of the dissolution or growth curve is usually connected with the so-called order of the process, e.g. linear time dependence of the dissolution rate (when data is plotted as the logarithm of the release or crystallized amount of drug versus time) denotes a first order process, or the process where pharmaceutical dosage of a released drug proportional to the amount of drug released by a unit time interval, diminishes.

Figure 3B:
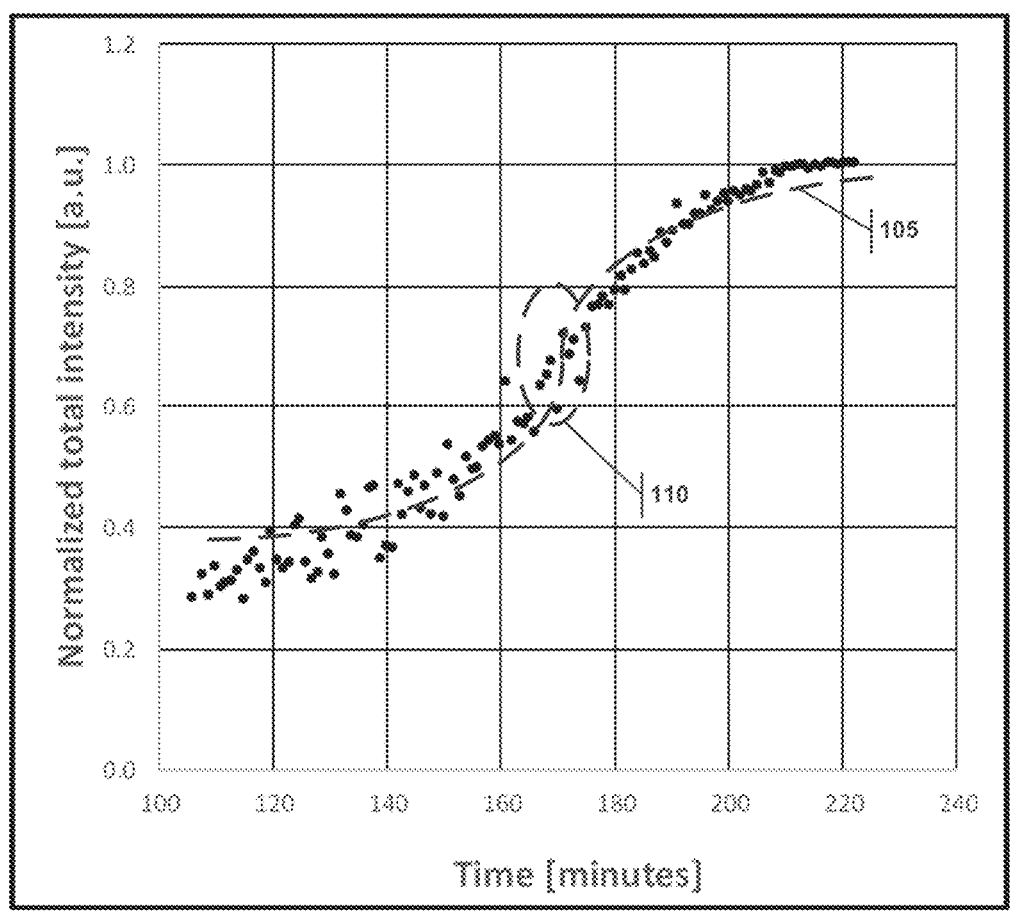
FIG. 3B is a graph showing the normalized total intensity of the particles in a colloidal solution vs. time, illustrating growth or crystallization.
Figure 3C:
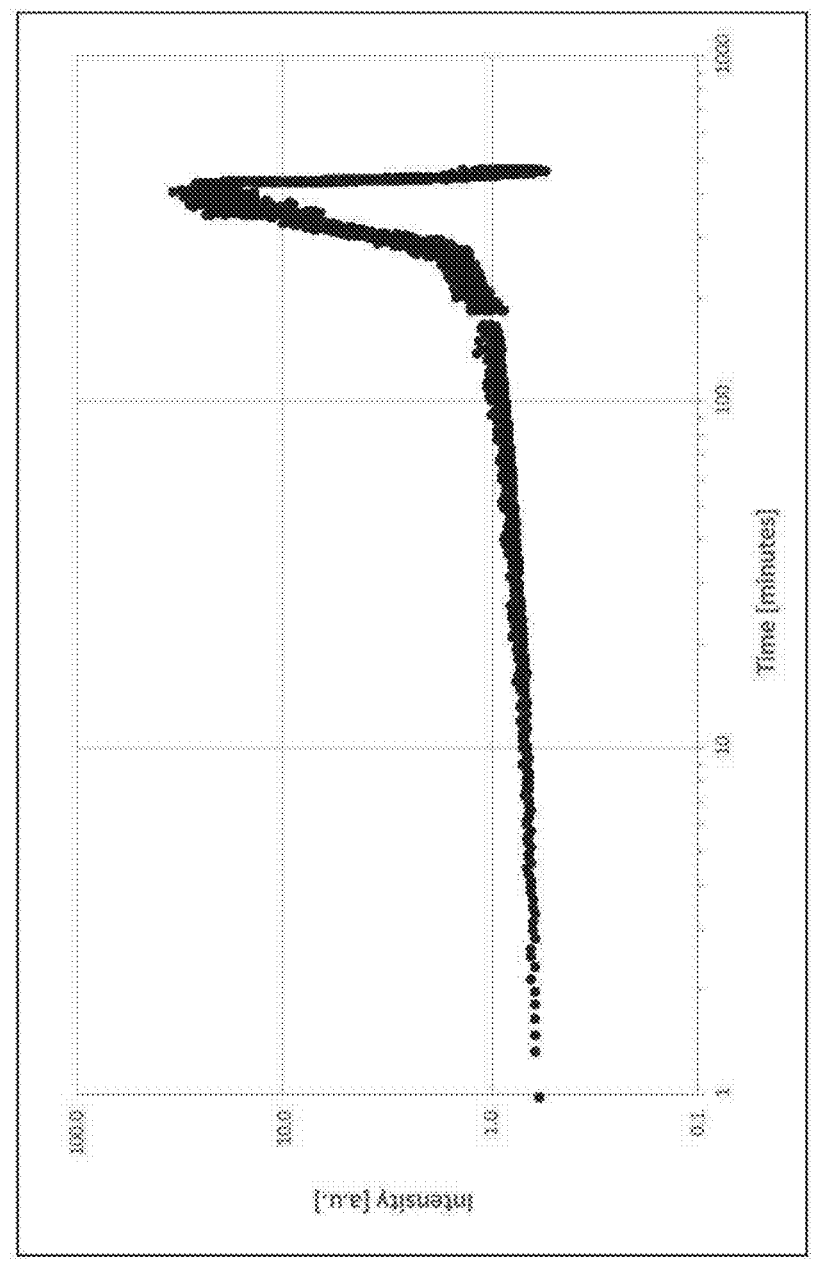
FIG. 3C is a graph showing the normalized total intensity of the particles in a colloidal solution vs. time, illustrating growth or crystallization and subsequent dissolution.

FIG. 3B illustrates the normalized intensity plotted against time of a different colloidal solution, which indicates that the particles are growing—i.e., crystallizing or aggregating. Line 105 is the best fit for this particular plot. The line 105 has an inflection point at region 110, suggesting that there is a significant amount of crystallization or aggregation during this time. FIG. 3C is yet another plot of intensity against time for another colloidal solution, indicating crystallization or aggregation and then dissolution after changes to the colloid (like the addition of some salt that changed pH) have been introduced.

Figure 4:
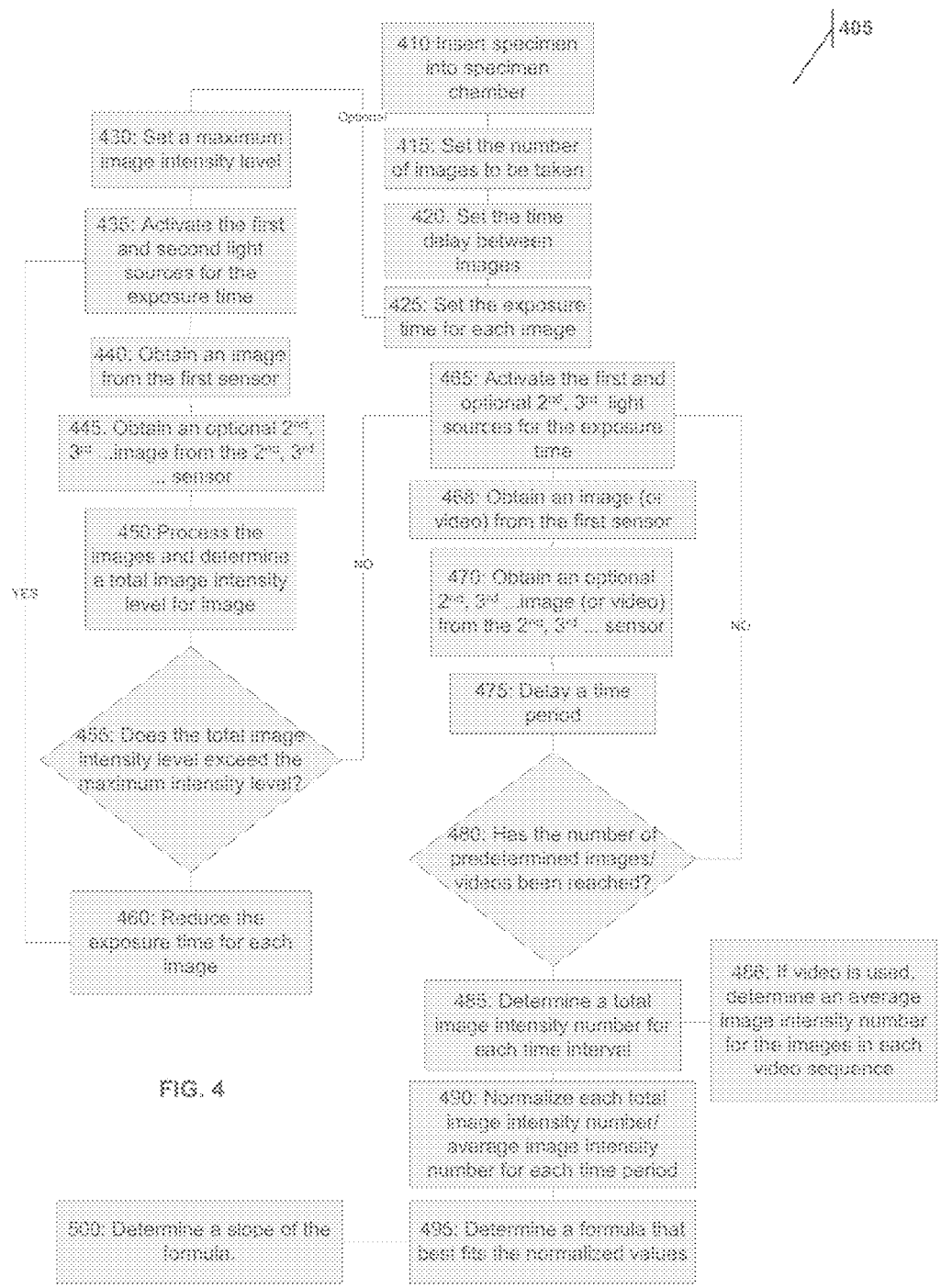
FIG. 4 is a flowchart depicting a method for determining the growth/dissolution rate of colloidal particles.

Now turning to FIG. 4, a method 405 for determining the growth/dissolution rate of colloidal particles will be described. It should be noted that this method is described in steps, but it will be apparent to those in the art that the order of steps can be changed and still fall within the scope of the claims below.

At step 410 a colloidal solution is inserted into the specimen chamber, e.g. the cuvette. Steps 415, 420, and 425 set a number of variables for the measurements including the number of images to be taken, the time delay between the images, and the exposure time. The combination of the delay between images and the number of images to be taken defines the measurement window. This can be pre-set or, as described below, it can be dynamic.

The method may have optional steps 430-460 that address the sensitivity of the system. Specifically, at step 430 a maximum image intensity level is set, and in steps 435-445 the light sources are activated, and the images are captured to determine a total image intensity level for the image at step 450. If at step 455 the total image intensity level from step 450 exceeds the maximum image intensity level, then the system will reduce the exposure time at step 460 and repeat the steps 435-455 until the total image intensity level is below the maximum, at which time the system begins at step 465 to obtain the image and intensity levels from which a growth/dissolution rate will be determined. This helps prevent the large particles from over saturating the image, which tends to blind the system from the smaller particles, which would in turn negatively affect the efficiency and range of the system.

Steps 430-460 can be omitted as optional, and the method can proceed directly from step 425 to step 465, which activates the first and second light sources (or the single light source if a single light source apparatus setup such as that shown in FIG. 1A is used) for the exposure time (step 465), obtaining a first and second images (or a single image in a single light source apparatus setup) (steps 468 and 470). The system then delays for the preset time period between images and determines at step 480 if the number of images has been reached. If the total number of images has been reached, then a total image intensity level for each image is determined and normalized (steps 485 and 490), and a formula that fits the normalized values is determined (step 95), from which a slope may be calculated (step 500). The normalization process comprises finding the largest intensity (count) of all pixels in the image and then dividing all intensities (counts) in this run by that number.

The method 405 may be more robust by obtaining a short video instead of a single image at steps 468 and 470. If this is done, then at step 486 an average intensity number for each of the videos in the sequence may be calculated (i.e., summed intensity of each frame/image in the video divided by the number of frames/images in the video) for each time interval, and that value is then normalized. By performing step 486, the method 405 can take images or videos at each time interval and will not unfairly weigh one in the normalization. Alternatively, if the method 405 is using only videos, and each video is comprised of the same number of frames/images, then the intensity of all the pixels in all the frames/images in each video may be used and normalized, thus skipping step 486.

It should be noted that the system may not set a total number of images/videos to be reached (i.e., step 415); rather, the system could set a total elapsed time, and step 480 can check if the elapsed time has been met. Furthermore, the processor may determine the total image intensity values and the slope nearly simultaneously while taking the images (i.e., after step 470). This allows the system to have a dynamic total measurement window. Specifically, if the solution is decreasing for the first minute at a substantial rate which then stabilizes to a nearly linear function (as in FIG. 3A), the method could perform steps 485-500 nearly simultaneously while taking the images (i.e., after step 470), and step 480 could be based on a query as to whether the determined slope is changing. If it is not changing, the method could stop measuring.

It should also be noted that the delay between the images/videos may also be dynamic. For example, if the processor determines the total image intensity values and the slope nearly simultaneously while taking the images (i.e., after step 470), it can nearly simultaneously determine the slope. If that slope is large or changing rapidly (as the first part of the graph in FIG. 3A), then it might be advantageous to decrease the delay time between subsequent images/videos—in other words taking more sample images/videos when the colloidal solution is changing quickly. This would allow the system to more precisely measure the slope when the growth/dissolution rate is most volatile. When the rate begins to steady and become less volatile, then the delay between images/videos can be increased.

While the embodiments herein have referred to nanoparticles, the same methods and devices disclosed herein can also be applied to particles that are larger—for example, micron-sized and larger (even greater than 100 microns); thus, the claims below are not to be limited to solely nanoparticles.

Although exemplary embodiments and applications of the invention have been described herein including as described above and shown in the included example Figures, there is no intention that the invention be limited to these exemplary embodiments and applications or to the manner in which the exemplary embodiments and applications operate or are described herein. Indeed, many variations and modifications to the exemplary embodiments are possible as would be apparent to a person of ordinary skill in the art. The invention may include any device, structure, method, or functionality, as long as the resulting device, system or method falls within the scope of one of the claims that are allowed by the patent office based on this or any related patent application.

The invention claimed is:

1. A system for determining the growth/dissolution rate of colloidal particles, the system comprising:
   a light source constructed to emit a sheet of electromagnetic radiation at a specimen chamber wherein the sheet defines a plane, wherein the chamber is constructed to hold the colloidal particles and to allow a portion of the sheet to scatter from the particles;
   a sensor positioned offset from the plane to observe the scattered portion of the sheet, wherein the sensor is adapted to detect the electromagnetic radiation;
   a processor connected to the sensor, the processor configured to perform the following steps:
   a. activating the light source;
   b. obtaining an image from the sensor, wherein the image comprises an array of pixels, and each pixel is assigned an intensity level representing the intensity of the electromagnetic radiation detected at the pixel position;
   c. repeating step (b) at a time interval;
   d. for each image obtained in step (b), determining a total image intensity level by summing the intensity levels of the pixels in the image;
   e. normalizing the total image intensity level for each image determined in step (d);
   f. calculating a formula that fits the normalized values of step (e); and
   g. calculating a slope of the formula of step (f).

2. The system of claim 1, wherein the image in step (b) comprises a video with a plurality of images.

3. The system of claim 2, wherein the total image intensity level comprises determining an average intensity level of the plurality of images within each video.

4. The system of claim 1, wherein the processor is further configured to perform the following steps:
   setting a measurement window; and
   repeating step (c) until the measurement window is reached.

5. The system of claim 4, wherein the measurement window is based on a total elapsed time or total number of images obtained.

6. The system of claim 4, wherein the measurement window is based on the slope as calculated from step (g).

7. The system of claim 1, wherein the time interval is based on the slope as calculated from step (g).

8. The system of claim 1, wherein when the slope as calculated from step (g) is negative, it indicates dissolution of the colloidal particles, and when it is positive, it indicate growth the colloidal particles.

9. A system for determining the growth/dissolution rate of colloidal particles, the system comprising:
   a first light source constructed to emit a first beam of electromagnetic radiation at substantially a first wavelength;
   a second light source constructed to emit a second beam of electromagnetic radiation at substantially a second wavelength;
   the first and second beams are combined into a combined sheet and the combined sheet is directed at a specimen chamber wherein the sheet defines a plane, the chamber is constructed to hold the colloidal particles and to allow a portion of the combined sheet to scatter from the particles;
   a first sensor and a second sensor positioned offset from the plane to observe the scattered portion of the combined sheet, wherein the first sensor biased to detect electromagnetic radiation at substantially the first wavelength and the second sensor biased to detect electromagnetic radiation at substantially the second wavelength;
   a processor connected to the first and second sensors, the processor configured to perform the following steps:

a. activating the first and second light sources;
b. obtaining an image from the first and second sensors, wherein the image comprises an array of pixels, and each pixel is assigned an intensity level representing the intensity of the electromagnetic radiation detected at the pixel position;
c. repeating step (b) at a time interval;
d. for each image obtained in step (b) determining a total image intensity level by summing the intensity levels of the pixels in the image;
e. normalizing the total image intensity level for each image determined in step (d);
f. calculating a formula that fits the normalized values of step (e); and
g. calculating a slope of the formula of step (f).

10. The system of claim 9, wherein the image in step (b) comprises a video with a plurality of images.

11. The system of claim 10, wherein the total image intensity level comprises determining an average intensity level of the plurality of images within each video.

12. The system of claim 9, wherein the processor is further configured to perform the following steps:
setting a measurement window; and
repeating step (c) until the measurement window is reached.

13. The system of claim 12, wherein the measurement window is based on a total elapsed time or total number of images obtained.

14. The system of claim 12, wherein the measurement window is based on the slope as calculated from step (g).

15. The system of claim 9, wherein the time interval is based on the slope as calculated from step (g).

16. The system of claim 9, wherein when the slope as calculated from step (g) is negative it indicates dissolution of the colloidal particles, and when it is positive, it indicate growth the colloidal particles.

17. The system of claim 9, further comprising:
a third light source constructed to emit a third beam of electromagnetic radiation at substantially a third wavelength, wherein the third beam is combined into the combined sheet;
the scattered portion of the combined sheet is further directed at a third sensor biased to detect electromagnetic radiation at substantially the second wave length; and wherein the processor is connected to the third sensor and wherein step (b) further comprises obtaining an image from the third sensor.

18. The system of claim 9, wherein the first and second light sources are a single light source.

19. The system of claim 9, wherein the first and second sensors are a single sensor.

20. The system of claim 9, wherein the first and second beams are combined by way of a combining structure.

21. The system of claim 9, wherein the scattered portion of the combined sheet is de-combined by a beam splitter prior to reaching the first or second sensor.

22. The system of claim 9, wherein the processor is further configured to perform the following steps:
setting a maximum image intensity level; and
adjusting an exposure time of the sensors if the total image intensity level exceeds the maximum intensity level.

23. A method for determining the growth/dissolution rate of colloidal particles, the method comprising:
a. providing a light source constructed to emit a sheet of electromagnetic radiation at a specimen chamber wherein the sheet defines a plane, wherein the chamber is constructed to hold the colloidal particles and to allow a portion of the beam to scatter from the particles, the scattered portion of the sheet is directed to a sensor that is positioned offset from the plane, and wherein the sensor is adapted to detect the electromagnetic radiation;
b. activating the light source;
c. obtaining an image from the sensor, wherein the image comprises an array of pixels, and each pixel is assigned an intensity level representing the intensity of the electromagnetic radiation detected at the pixel position;
d. repeating step (c) at a time interval;
e. for each image obtained in step (c), determining a total image intensity level by summing the intensity levels of the pixels in the image;
f. normalizing the total image intensity level for each image determined in step (e);
g. calculating a formula that fits the normalized values of step (f); and
h. calculating a slope of the formula of step (g).

* * * * *